(12) United States Patent
Kuntz et al.

(10) Patent No.: US 11,311,661 B2
(45) Date of Patent: Apr. 26, 2022

(54) OPHTHALMIC PRESSURE CONTROL SYSTEM, A KIT OF PARTS AND A METHOD

(71) Applicant: D.O.R.C. Dutch Ophthalmic Research Center (International) B.V., Zuidland (NL)

(72) Inventors: John Peter Kuntz, Papendrecht (NL); Andrés Alberto Alvarez Cabrera, Delft (NL); Wim Rosenquist, Hellevoetsluis (NL)

(73) Assignee: D.O.R.C. DUTCH OPHTHALMIC RESEARCH CENTER (INTERNATIONAL) B.V., Zuidland (NL)

(*) Notice: Subject to any disclaimer, the term of this patent is extended or adjusted under 35 U.S.C. 154(b) by 121 days.

(21) Appl. No.: 16/297,080

(22) Filed: Mar. 8, 2019

(65) Prior Publication Data
US 2019/0275220 A1 Sep. 12, 2019

(51) Int. Cl.
*A61F 9/007* (2006.01)
*A61M 1/00* (2006.01)
(Continued)

(52) U.S. Cl.
CPC .......... *A61M 1/85* (2021.05); *A61F 9/00736* (2013.01); *A61M 1/0058* (2013.01); *A61B 3/16* (2013.01);
(Continued)

(58) Field of Classification Search
CPC ............... A61B 3/16; A61F 2250/0013; A61F 9/00736; A61M 1/0058; A61M 2205/3334; A61M 2210/0612
See application file for complete search history.

(56) References Cited

U.S. PATENT DOCUMENTS

| 4,841,984 A | 6/1989 | Armeniades et al. |
| 5,157,603 A | 10/1992 | Scheller |

(Continued)

FOREIGN PATENT DOCUMENTS

| DE | 29610416 | 10/1996 |
| DE | 29610419 | 10/1996 |

(Continued)

OTHER PUBLICATIONS

Search Report from Netherlands Application No. 2020558 dated Mar. 9, 2018.
(Continued)

*Primary Examiner* — Deanna K Hall
(74) *Attorney, Agent, or Firm* — Adsero IP

(57) ABSTRACT

The invention relates to an ophthalmic pressure control system, comprising: a pressure regulator having an input port and an output port, and an infusion line having a proximal end and a distal end, the proximal end being connected to the output port of the pressure regulator, and the distal end being detachably connected to an ophthalmic irrigation module. Further, the system includes a control unit driving the pressure regulator for controlling an infusion fluid pressure at a distal end of the ophthalmic irrigation module. The control unit is arranged for performing a fluid calibration process including a step of determining a fluid impedance of the ophthalmic irrigation module. The infusion line is associated with a kit of parts including a first and a second ophthalmic irrigation device, or the ophthalmic irrigation module is an ophthalmic irrigation device for surgical use.

5 Claims, 2 Drawing Sheets

Figure 1:
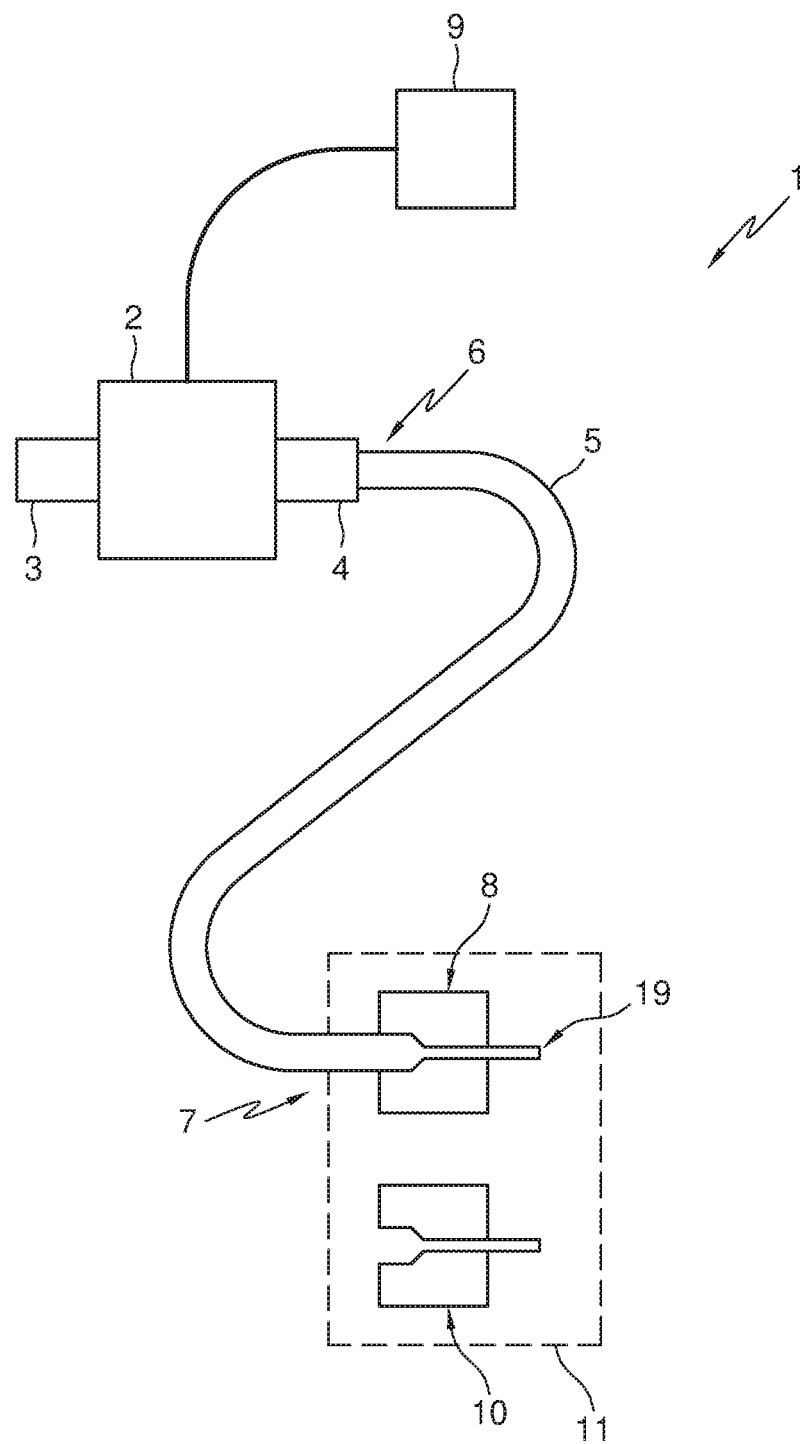

(51) Int. Cl.
*A61B 3/16* (2006.01)
*A61B 5/03* (2006.01)

(52) U.S. Cl.
CPC ......... *A61B 5/036* (2013.01); *A61F 2250/006* (2013.01); *A61F 2250/0013* (2013.01); *A61M 1/74* (2021.05); *A61M 2205/3334* (2013.01); *A61M 2210/0612* (2013.01)

(56) References Cited

U.S. PATENT DOCUMENTS

| | | | |
|---|---|---|---|
| 2004/0097870 | A1 | 5/2004 | Kadziauskas et al. |
| 2005/0209621 | A1 | 9/2005 | Gordon |
| 2005/0245909 | A1 | 11/2005 | McCary |
| 2007/0010730 | A1 | 1/2007 | Gordon |
| 2009/0247938 | A1 | 10/2009 | Buboltz |
| 2016/0346123 | A1* | 12/2016 | Koplin ................ A61M 3/0212 |
| 2017/0224888 | A1 | 8/2017 | Hickey |

FOREIGN PATENT DOCUMENTS

| | | |
|---|---|---|
| EP | 1647248 A1 | 4/2006 |
| EP | 2065020 | 6/2009 |
| EP | 1895958 B1 | 8/2009 |
| EP | 2538900 A1 | 1/2013 |
| EP | 2538900 B1 | 12/2017 |
| JP | H01-207059 | 8/1989 |
| JP | H04-504514 A | 8/1992 |
| JP | H08-010281 A | 1/1996 |
| JP | 2004-507321 A | 3/2004 |
| WO | WO 1997/047339 | 12/1997 |
| WO | WO 2007/001859 | 1/2007 |
| WO | WO 2007/001929 | 1/2007 |
| WO | WO 2007/037894 | 4/2007 |
| WO | WO 2007/149667 | 12/2007 |
| WO | WO 2009/017921 | 2/2009 |
| WO | WO 2011/105909 | 9/2011 |
| WO | WO 2013/079959 | 6/2013 |

OTHER PUBLICATIONS

Alcon publication (2008) Alcon, Inc., CON058, "Constellation Vision System".
Centurion Brochure (2013) Centurion Vision System: Optimizing Every Moment, PHUN210, Aug. 2013, Alcon, Novartis Company13073SK.
Holden (2007) The Phaco Fluidics Book, pp. 1-116.
Riemann and Miller (2009) pp. 1-4, "True" IOP Control: A Constellation Vision System Advanced Technology, available at: http://www.visioncareprofessional.com/emails/alcon/18/Constellation_IOP_advert.pdf.
Spirochkin (2013) Cataract Surgery, Edited by Farhan Zaidi, published by Intech, downloaded from: http://www.intechopen.com/books/cataract-surgery; Chapter 9, p. 121-136, "Hydrodynamic Analysis and Irrigation Device Design for the Coaxial and Bimanual Phacoemulsification Techniques in Cataract Surgery".
International Search Report from PCT/NL2011/050139 dated Aug. 8, 2011.
Notice of Abandonment from U.S. Appl. No. 13/581,030 dated Jan. 11, 2017.
Office Action from JP App No. 2012-554956 dated Sep. 8, 2015 with English translation.
Office Action from U.S. Appl. No. 13/581,030 dated Jan. 16, 2015.
Office Action from U.S. Appl. No. 13/581,030 dated Aug. 13, 2015.
Office Action from U.S. Appl. No. 13/581,030 dated Feb. 12, 2016.
Office Action from U.S. Appl. No. 13/581,030 dated Jun. 30, 2016.

* cited by examiner

OPHTHALMIC PRESSURE CONTROL SYSTEM, A KIT OF PARTS AND A METHOD

RELATED APPLICATIONS

This application claims priority to and the benefit of Netherlands Application No. 2020558, filed on Mar. 9, 2018, entitled "An Ophthalmic Pressure Control System, A Kit of Parts and a Method", which is incorporated herein by reference in its entirety.

The invention relates to an ophthalmic pressure control system, comprising a fluid pressure regulator having an input port and an output port, an infusion line having a proximal end and a distal end, the proximal end being connected to the output port of the pressure regulator, and the distal end being detachably connected to an ophthalmic irrigation module, and a control unit driving the pressure regulator for controlling an infusion fluid pressure at a distal end of the ophthalmic irrigation module.

In ophthalmic surgery, small probes are inserted into an eye, via an insert opening e.g. a cannula through the pars plana of the eye, to cut, remove or otherwise manipulate tissue. Typically, the interior of the eye is flushed with an infusion fluid by flowing the fluid into the eye via an ophthalmic irrigation module penetrating the eye. The irrigation module is fed by an infusion line that is pressurized by a fluid pressure regulator. During manipulating tissue in the interior of the eye, the amount of fluid leaving the eye via the insert opening can vary over time, e.g. depending on surgical acts.

In prior art systems, the fluid flow towards the eye may be controlled using a control unit that drives the pressure regulator for controlling an infusion fluid pressure at a distal end of the ophthalmic irrigation module. The controlling process can be based on a sensed fluid pressure in the interior of the eye. As an alternative, European patent EP 2 538 900 B1 in the name of the same applicant discloses that the fluid pressure is estimated without use of a fluid pressure sensor.

It is an object of the present invention to provide an ophthalmic pressure control system wherein a process of controlling an infusion fluid pressure at a distal end of the ophthalmic irrigation module is improved. Thereto, according to the invention, the control unit is arranged for performing a fluid calibration process including a step of determining a fluid impedance of the ophthalmic irrigation module, wherein either the infusion line is associated with a kit of parts, comprising a first ophthalmic irrigation device for surgical use, the kit of part further comprising a second ophthalmic irrigation device for calibration use, such that the ophthalmic irrigation module detachably connected to the infusion line is the second ophthalmic irrigation device of the kit of parts, or wherein the ophthalmic irrigation module is an ophthalmic irrigation device for surgical use.

By performing a calibration process, a static and/or dynamic fluid response to an action of the pressure regulator can be evaluated, thereby improving the system to compensate for a pressure loss in the interior of the eye due to surgical acts in the eye, e.g. in terms of compensation speed and accuracy, e.g. for setting the fluid pressure in the eye to a pre-defined set point.

According to an aspect of the invention, an insight is exploited that the fluid impedance of the ophthalmic irrigation module may have a significant contribution to the fluidal behaviour of the ophthalmic pressure control system, due to the relatively small dimensions of the irrigation module. By determining a fluid impedance of the ophthalmic irrigation module, the overall fluid response of the system can be estimated more accurately, thereby further improving the pressure controlling process.

By using the system according to the invention, an intraocular eye pressure can be kept stable at a value set by the surgeon, regardless of any surgical procedure.

Further, by associating the infusion line with a kit of parts, comprising a first ophthalmic irrigation device for surgical use, the kit of parts further comprising a second ophthalmic irrigation device for calibration use, such that the ophthalmic irrigation module detachably connected to the infusion line is the second ophthalmic irrigation device of the kit of parts, the control unit can perform the fluid calibration process including the step of determining the fluid impedance of the irrigation module without being physically connected to the first irrigation device that is actually used in a surgery process. Then, the calibration process can be performed while the second irrigation device for surgical use is located elsewhere, e.g. in a surgical position e.g. penetrating the eye. After the calibration process has finalized, the first irrigation device for calibration use can be replaced by the irrigation device for surgical use, while still in the surgical position, thereby minimizing surgical acts.

Advantageously, the determined fluid impedance can be compared with a multiple number of predetermined fluid impedance calibration reference values associated with corresponding types of ophthalmic irrigation devices. As the ophthalmic irrigation device that is used during calibration in practice belongs to a set including a limited number of device types, e.g. depending on a geometry and/or size of the device, the fluid impedance determination can be used for identifying the type of the device to be used in a surgery process, i.e. the first device. The fluid impedance calibration reference values can be measured in advance, during laboratory conditions and/or using dedicated measuring sensors, and can be provided together with the first and second device, e.g. in a digital manner with documentation of the device. Then, an identification of the device at hand can be obtained without a very precise determination of the fluid impedance. In principle, even a relatively rough, inaccurate determination of the fluid impedance of the second device may be useful for identifying the type of the first device, especially if a comparison with the multiple number of predetermined fluid impedance calibration reference values can be performed with a positive result within a high probability regime. If the fluid impedance value that is determined during the calibration process matches, within a chosen probability interval, with a specific reference value of the multiple number of predetermined fluid impedance calibration reference values, a positive identification can be made with an ophthalmic irrigation device type associated with said reference value. Then, upon identifying the type of the first device, known fluid impedance information of said identified first device can advantageously be used for evaluating a static and/or dynamic fluid response to an action of the pressure regulator, even when a relatively global or rough determination of the fluid impedance is performed during the calibration process.

The predetermined fluid impedance calibration reference values may match with the fluid impedances of the corresponding types of first ophthalmic irrigation devices. Then, the first and second ophthalmic irrigation device of the kit of parts have the same fluid impedance, and the matched predetermined fluid impedance calibration reference value can be used for evaluating the fluid response.

Alternatively, the predetermined fluid impedance calibration reference values are different from but in a unique manner related to the fluid impedances of the corresponding types of the first ophthalmic irrigation devices. Then, the first and second ophthalmic irrigation device of the kit of parts have a mutually different fluid impedance, however mutually related in a unique manner. The device type can be determined by determining the fluid impedance of the second ophthalmic irrigation device and relating the determined fluid impedance value of the second device to the corresponding type of the first ophthalmic irrigation device. The step of relating the determined fluid impedance value to the type of the corresponding first ophthalmic irrigation device can be applied by using information of the relationship between the predetermined fluid impedance calibration reference values on the one hand and the fluid impedances of the corresponding types of the first ophthalmic irrigation devices on the other hand. Said information can be available in any way, e.g. as a table.

By relating the predetermined fluid impedance calibration reference values in a unique manner to different fluid impedance values of the corresponding first devices, the fluid impedance of the first and second device in the kit of parts differ from each other in a unique, known manner. Then, the fluid impedance of the second device that is used for calibration can be set to an impedance regime that can be measured quickly, thereby saving calibration time. As an example, the second device of a kit of parts may have a fluid impedance that is significant lower than the fluid impedance of the first device.

The first ophthalmic irrigation device may include an actuator mechanism, e.g. including a phaco needle and sleeve, while the second ophthalmic irrigation device is a passive device. However, the first irrigation device may be identical to the second irrigation device, e.g. both devices including an actuator mechanism or both devices being passive, e.g. implemented as an infusion cannula.

Alternatively, the ophthalmic irrigation module that is detachably connected to the distal end of the infusion line, during the calibration process, is an ophthalmic irrigation device for surgical use. Then, the calibration process including the step of determining a fluid impedance of the ophthalmic irrigation module can be performed probing a device for surgical use, even when the device is located in a position penetrating the eye.

Also in this embodiment, the determined fluid impedance can be compared with a multiple number of known predetermined fluid impedance calibration reference values associated with corresponding types of ophthalmic irrigation devices, thereby relaxing accuracy requirements to the fluid impedance determination.

In addition, the invention relates to a kit of parts.

The invention also relates to a method of controlling an infusion fluid pressure.

Further, the invention relates to a computer program product. A computer program product may comprise a set of computer executable instructions stored on a data carrier, such as a CD or a DVD. The set of computer executable instructions, which allow a programmable computer to carry out the method as defined above, may also be available for downloading from a remote server, for example via the Internet.

Further advantageous embodiments according to the invention are described in the following claims.

It should be noted that the technical features described above or below may each on its own be embodied in a system or method, i.e. isolated from the context in which it is described, separate from other features, or in combination with only a number of the other features described in the context in which it is disclosed. Each of these features may further be combined with any other feature disclosed, in any combination.

Figure 2:
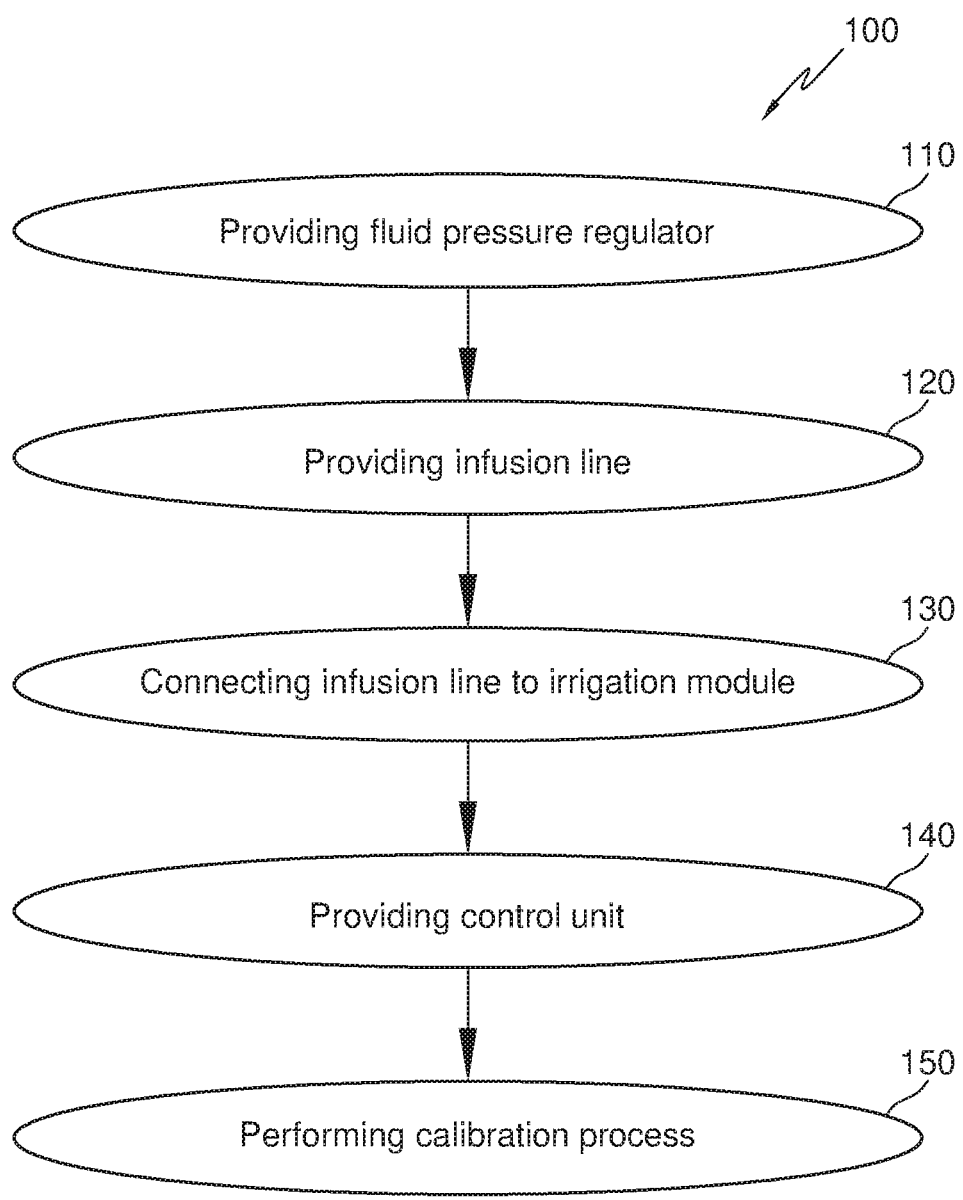

The invention will now be further elucidated on the basis of a number of exemplary embodiments and an accompanying drawing. In the drawing:

FIG. 1 shows a schematic view of an ophthalmic pressure control system according to the invention, and FIG. 2 shows a flow chart of a method according to the invention.

It is noted that the figures show merely preferred embodiments according to the invention. In the figures, the same reference numbers refer to equal or corresponding parts.

FIG. 1 shows a schematic view of an ophthalmic pressure control system 1 according to the invention. The system 1 includes a fluid pressure regulator 2 having an input port 3 and an output port 4. The system 1 is also provided with an infusion line 5 having a proximal end 6 and a distal end 7, the proximal end 6 being connected to the output port 4 of the pressure regulator 2. In the shown embodiment, the distal end 7 of the infusion line 5 is detachably connected to an ophthalmic irrigation module 8. The infusion line 5 can be implemented as a so-called high flow infusion line. Further, the system 1 includes a control unit 9 driving the pressure regulator 2 for controlling an infusion liquid pressure at a distal end 19 of the ophthalmic irrigation module 8.

During operation of the system 1, the distal end 19 of the ophthalmic irrigation module 8 penetrates into the interior of a patient's eye for flowing an irrigation fluid into said interior of the eye. By flowing irrigation fluid into the eye, any internal pressure loss in the eye, due to surgical acts in the eye, may be compensated. Upon activating the fluid pressure regulator 2, an irrigation fluid pressure is exerted, at the distal end 19 of the ophthalmic irrigation module 8. During operation of the system, the control unit 9 drives the pressure regulator 2 so as to control the infusion fluid pressure at the distal end 19 of the ophthalmic irrigation module 8.

For the purpose of regulating a fluid pressure, through the infusion line 5, the fluid pressure regulator 2 may be provided with an infusion bottle feeding the fluid pressure regulator 2 infusion line 5 via a drip chamber connected to the input port 3 of the fluid pressure regulator 2.

The control unit 9 is further arranged for performing a fluid calibration process including a step of determining a fluid impedance of the ophthalmic irrigation module 8, such that the control unit may statically and/or dynamically control the infusion fluid pressure at the distal end 19 of the ophthalmic irrigation module 8. By characterizing a fluid impedance of the ophthalmic irrigation module 8 provided with an internal passage for flowing the irrigation fluid towards the interior of the eye, a static and/or dynamic response of the ophthalmic irrigation module 8 can be estimated, thereby improving a fluid pressure control at the distal end of the module, during surgery in the eye. When performing an eye pressure compensation process, a desired fluid flow characteristic can be set, e.g. in terms of volume and time taking into account the fluid system behaviour of the calibrated system.

In a first embodiment, shown in FIG. 1, the ophthalmic irrigation module 8 is a passive device having the same fluid impedance as a corresponding ophthalmic irrigation device 10 including an actuator mechanism to be used for surgical activities. The actuator mechanism may e.g. include a phaco needle and sleeve. The fluid impedance of the irrigation module may depend on dimensions and/or geometry of an internal fluid passage through the irrigation module, e.g. length, diameter, curves etc. By using a passive counterpart 8 of the corresponding active ophthalmic irrigation device 10, the control unit 9 can perform the fluid calibration process including the step of determining the fluid impedance of the ophthalmic irrigation module 8 without being physically connected to the irrigation device 10 itself. The passive ophthalmic irrigation module 8 may serve as a mock module suitable for performing a fluid calibration procedure.

In practice, the ophthalmic irrigation device 10, e.g. the phaco sleeve, can remain in a position penetrating the eye, e.g. traversing a cannula that is present in the conjunctiva/sclera of the eye. Then, the passive counterpart 8 of the active irrigation device can be detachably connected to the infusion line 5 for performing the calibration process, and, subsequently, the passive irrigation module 8 can be removed from said infusion line 5 while the active irrigation device 10 is then detachably connected to the infusion line 5, for operationally providing the infusion fluid into the interior of the eye, in a controllably manner. In other words, the passive ophthalmic irrigation module 8 detachably connected to the infusion line 5 is replaced by a corresponding ophthalmic irrigation device 10 having the same fluid impedance but including an actuator mechanism.

In FIG. 1, the passive ophthalmic irrigation module 8 is connected to the distal end 7 of the infusion line 5, while the active irrigation device 10 is not connected. The passive irrigation module 8 and the active irrigation device 10 have the same or similar fluid impedance, measured from a proximal end of the module 8, 10, thus forming a set of related ophthalmic modules, or a kit of parts 11. The kit of parts 11 comprises a first ophthalmic irrigation device 10 for surgical use, including an actuator mechanism, and further comprises a second ophthalmic irrigation device 8 for calibration use, implemented as a passive device having the same fluid impedance as the first ophthalmic irrigation device 10. The first ophthalmic irrigation device 10 is intended for surgical use, e.g. for placing in or on the eye, while the second ophthalmic irrigation device 8 serving as a dummy module 8 is intended for determining a fluid impedance of the first device 10. The second ophthalmic irrigation device 8 may be implemented as a disposable tool, e.g. a dummy cannula, that can be pre-assembled on the distal end 7 of the infusion line 5, as a representative tool of the actual device 10. During a calibration process, a fluid resistance of the tool 8 can be measured. Then, the tool 8 can be removed, and the infusion line 5 is in principle ready for surgical use.

A kit of parts may be provided for each gauge size of a specific ophthalmic device, e.g. for each cannula gauge size. Further, the first and second device of each kit of parts have the same or similar fluid impedance meaning that the tolerances of the internal passage geometry of the pair of devices are with certain limits such that the estimated intraocular pressure is with pre-specified limits.

It is noted that also the first ophthalmic irrigation device 10 can be implemented as a passive device, without an actuator, e.g. as an infusion cannula to be inserted into the eye. Then, the ophthalmic irrigation device used during the fluid impedance determining step can be identical to another ophthalmic irrigation device connected to the distal end of the infusion line after finalizing the fluid impedance determining step, i.e. during surgery. In this case, the kit of parts 11 may include two identical ophthalmic irrigation devices, viz. a first ophthalmic irrigation device 10 that is used for performing surgical acts, e.g. for placing in or on the eye, and a second ophthalmic irrigation device 8 that is used for determining the fluid impedance of the devices. It is noted that the two identical ophthalmic irrigation devices may be both passive, i.e. without any actively driven component or actuator mechanism, or may be both active, i.e. including an actively driven component or actuator mechanism.

Thus, the infusion line 5 can be is associated with a kit of parts, comprising a first ophthalmic irrigation device 10 for surgical use, the kit of part further comprising a second ophthalmic irrigation device 8 for calibration use, the first and the second ophthalmic irrigation devices 10, 8 having the same fluid impedance, such that the ophthalmic irrigation module detachably connected to the infusion line 5 is the second ophthalmic irrigation device 8 of the kit of parts.

Advantageously, the determined fluid impedance of the second device 8 is compared with a multiple number of predetermined fluid impedance calibration reference values reflecting the fluid impedances of the second devices and associated with corresponding types of first ophthalmic irrigation devices 10. If a predetermined fluid impedance calibration reference value can be found that is the same as the determined fluid impedance of the second device 8, within pre-specified limits, the type of the first device 10 is identified and said predetermined fluid impedance calibration reference value can be used for evaluating a static and/or dynamic fluid response to an action of the pressure regulator, even when a relatively global or rough determination of the fluid impedance is performed during the calibration process.

Alternatively, the predetermined fluid impedance calibration reference values, reflecting the fluid impedances of the second devices 8, are different from the fluid impedances of the corresponding types of the first ophthalmic irrigation devices 10, however being in a unique manner related to said types of the first devices 10. Again, the device type can be determined by determining the fluid impedance of the second ophthalmic device 8 and relating the determined fluid impedance value to the corresponding type of the first ophthalmic device, using information of the above-mentioned unique relationship that is available in some way, e.g. using a table or algorithm. As an example, the fluid impedance value of the second device 8 is at least an order lower than the fluid impedance value of the first device 10 saving calibration time if the first device impedance is relatively high.

It is noted that, as a further alternative, the determined fluid impedance of the second device 8 is not compared to predetermined reference values. Then, the determined fluid impedance itself can be used for evaluating a static and/or dynamic fluid response to an action of the pressure regulator.

In a second embodiment, the ophthalmic irrigation module detachably connected to the distal end of the infusion line is an ophthalmic irrigation device 10 for surgical use, optionally located in a position penetrating the eye. The device 10 may include an actuator mechanism. Then, the calibration process including the step of determining a fluid impedance of the ophthalmic irrigation module can be performed with the device 10 for surgical use, even when the device 10 is located in a position penetrating the eye.

Again, the determined fluid impedance of the device 10 can be compared with a multiple number of predetermined fluid impedance calibration reference values reflecting the fluid impedances of the devices, for the purpose of identifying the type of device at hand.

FIG. 2 shows a flow chart of a method according to the invention. The method is used for controlling an infusion liquid pressure at a distal end of an ophthalmic irrigation module. The method 100 comprises a step of providing 110 a fluid pressure regulator having an input port and an output port, a step of providing 120 an infusion line having a proximal end and a distal end, the proximal end being connected to the output port of the pressure regulator, a step of detachably connecting 130 the distal end of the infusion line to an ophthalmic irrigation module, a step of providing 140 a control unit driving the fluid pressure regulator for controlling an infusion fluid pressure at a distal end of the ophthalmic irrigation module, and a step of performing 150 a fluid calibration process including a step of determining a fluid impedance of the ophthalmic irrigation module, wherein the infusion line is associated with a kit of parts, comprising a first ophthalmic irrigation device for surgical use, the kit of part further comprising a second ophthalmic irrigation device for calibration use, the first and the second ophthalmic irrigation devices having the same fluid impedance, such that the ophthalmic irrigation module detachably connected to the infusion line is the second ophthalmic irrigation device of the kit of parts, or wherein the ophthalmic irrigation module is an ophthalmic irrigation device for surgical use.

The method may further comprise a step of disconnecting the second ophthalmic irrigation device. Then, the second ophthalmic irrigation device can be replaced by the first ophthalmic irrigation device.

The step of performing a fluid calibration process including a step of determining a fluid impedance of the ophthalmic irrigation module can be performed using dedicated hardware structures, such as FPGA and/or ASIC components. Otherwise, the method can at least partially be performed using a computer program product comprising instructions for causing a processor of a computer system to perform the above described step. A number of steps can in principle be performed on a single processor. However it is noted that at least one step can be performed on a separate processor, e.g. the step of determining a fluid impedance of the ophthalmic irrigation module.

The invention is not restricted to the embodiments described herein. It will be understood that many variants are possible.

These and other embodiments will be apparent for the person skilled in the art and are considered to fall within the scope of the invention as defined in the following claims. For the purpose of clarity and a concise description features are described herein as part of the same or separate embodiments. However, it will be appreciated that the scope of the invention may include embodiments having combinations of all or some of the features described.

The invention claimed is:

1. An ophthalmic pressure control system, comprising:
a fluid pressure regulator having an input port and an output port;
an infusion line having a proximal end and a distal end, the proximal end being connected to the output port of the fluid pressure regulator, and the distal end being detachably connected to an ophthalmic irrigation module, and
a control unit driving the fluid pressure regulator for controlling an infusion fluid pressure at a distal end of the ophthalmic irrigation module,
wherein the control unit is arranged for performing a fluid calibration process including a step of determining a fluid impedance of the ophthalmic irrigation module, and wherein the infusion line is associated with a kit of parts, comprising a first ophthalmic irrigation device for surgical use, the kit of parts further comprising a second ophthalmic irrigation device for determining a fluid impedance of the ophthalmic irrigation module for calibration use, wherein the ophthalmic irrigation module detachably connected to the infusion line is the second ophthalmic irrigation device of the kit of parts.

2. The ophthalmic pressure control system according to claim 1, wherein the first ophthalmic irrigation device includes an actuator mechanism and wherein the second ophthalmic irrigation device is a passive device.

3. The ophthalmic pressure control system according to claim 2, wherein the first ophthalmic irrigation device is provided with a phaco needle and sleeve.

4. The ophthalmic pressure control system according to claim 1, wherein the first ophthalmic irrigation device is identical to the second ophthalmic irrigation device.

5. The ophthalmic pressure control system according to claim 1, wherein the first and the second ophthalmic irrigation device of the kit of parts have the same fluid impedance.

* * * * *